US012642618B2

(12) United States Patent
O'Neal

(10) Patent No.: US 12,642,618 B2
(45) Date of Patent: Jun. 2, 2026

(54) CARRIERS FOR COLLECTING BIOLOGICAL SAMPLES

(71) Applicant: Sheridan O'Neal, Lockhart, TX (US)

(72) Inventor: Sheridan O'Neal, Lockhart, TX (US)

( * ) Notice: Subject to any disclaimer, the term of this patent is extended or adjusted under 35 U.S.C. 154(b) by 0 days.

(21) Appl. No.: 18/149,963

(22) Filed: Jan. 4, 2023

(65) Prior Publication Data

US 2024/0216101 A1 Jul. 4, 2024

(51) Int. Cl.
*A61B 50/36* (2016.01)
*A61B 50/30* (2016.01)
*A61B 50/37* (2016.01)
*A61M 5/00* (2006.01)
*A61M 5/32* (2006.01)

(52) U.S. Cl.
CPC .......... *A61B 50/36* (2016.02); *A61B 50/3001* (2016.02); *A61B 50/362* (2016.02); *A61B 50/37* (2016.02); *A61M 5/002* (2013.01); *A61M 5/3205* (2013.01)

(58) Field of Classification Search
CPC ... A61B 50/36; A61B 50/3001; A61B 50/362; A61B 50/37; A61M 5/002; A61M 5/3205
USPC ................................................ 206/569, 570
See application file for complete search history.

(56) References Cited

U.S. PATENT DOCUMENTS 4,932,533 A * 6/1990 Collier ................... C12M 23/48
206/370
5,011,020 A * 4/1991 Stevens ................. A45C 13/02
206/811

5,040,678 A * 8/1991 Lenmark, Sr. ....... B65D 81/107
206/443
5,405,012 A * 4/1995 Shindler ............ B65D 81/3827
220/592.25
5,449,071 A * 9/1995 Levy ................... A61B 10/0096
206/370
5,624,638 A * 4/1997 Negrotti ............. G09B 19/0069
206/229
6,116,426 A * 9/2000 Slonim .................. A61B 50/31
206/499
8,550,251 B1 * 10/2013 Ford ........................ A61J 1/16
206/370
9,016,449 B1 * 4/2015 Soboyejo ................ A45F 3/042
150/123
2002/0157972 A1 * 10/2002 Gallo ........................ A61J 1/00
206/570
2004/0031721 A1 * 2/2004 Mann ..................... A61B 10/04
206/570
2006/0060494 A1 * 3/2006 Goodman ........ A61B 5/150305
604/408
2007/0289894 A1 * 12/2007 Tennant ............. A61B 10/0096
206/569
2008/0121554 A1 * 5/2008 Townsend ................ A45C 5/06
206/570
2008/0141700 A1 * 6/2008 Fuchs ....................... F25D 3/08
206/570

(Continued)

*Primary Examiner* — Jacob K Ackun

(74) *Attorney, Agent, or Firm* — NORTON ROSE FULBRIGHT US LLP

(57) ABSTRACT

A carrier can comprise a case that defines an interior volume, a supply tray that defines a plurality of supply compartments, and a sample tray that defines one or more sample compartments and comprises a thermally-insulative material. The supply tray and the sample tray and each be removably coupled to the case in the interior volume.

20 Claims, 10 Drawing Sheets

(56)         References Cited

U.S. PATENT DOCUMENTS

| 2009/0053251 A1* | 2/2009 | Pogue-Caley | A61P 31/18 |
| | | | 435/372 |
| 2009/0291449 A1* | 11/2009 | Knapp, Jr. | B01L 3/545 |
| | | | 435/6.12 |
| 2011/0132911 A1* | 6/2011 | Zhang | B65D 77/0446 |
| | | | 206/459.5 |
| 2012/0228189 A1* | 9/2012 | Alhajri | G09B 23/00 |
| | | | 206/569 |
| 2017/0320054 A1* | 11/2017 | Crum | B01L 9/06 |
| 2023/0124963 A1* | 4/2023 | Laskin | A45C 5/065 |
| | | | 206/570 |
| 2024/0053341 A1* | 2/2024 | Giro Benet | G01N 33/57415 |

* cited by examiner

CARRIERS FOR COLLECTING BIOLOGICAL SAMPLES

TECHNICAL FIELD

The present invention relates generally to carriers for collecting biological samples.

BACKGROUND

Mobile phlebotomists travel to different locations to take one or more biological samples from individuals. Phlebotomists will typically bring supplies in simple tool boxes that are difficult to organize and may not offer adequate thermal insulation to store and preserve the biological samples that may need to be refrigerated or kept warm, particularly when the biological samples need to be transported over large distances. Accordingly, phlebotomists often need to bring a cooler along with the tool box. The inefficient organization of simple tool boxes and the need for multiple carriers to hold phlebotomy supplies and biological samples can be cumbersome and inefficient, which can lead to slow draw times.

SUMMARY

The present carriers can better organize medical supplies and store biological samples for efficient collection thereof with a case that can hold a supply tray and a sample tray. The supply tray can define a plurality of supply compartments capable of storing one or more supplies for collecting biological materials (e.g., one or more collection tubes, needles, wipes, bandages, and/or the like). The sample tray can define one or more sample compartments that can hold biological samples and can comprise a thermally-insulative material to maintain the temperature of the samples for transport. Both the supply tray and the sample tray can be removed from the case to provide access to supplies held in the supply compartments and to allow the biological samples to be placed in the sample compartment(s). In this manner, the carrier is capable of both carrying the supplies used for collecting biological samples in an organized manner and properly storing the biological samples for transport, allowing for more efficient collection of the biological samples.

Some of the present carriers for collecting biological samples comprise a case that defines an interior volume. Some carriers comprise a supply tray and a sample tray that are each removably coupled to the case in the interior volume. Some of the present kits comprise any of the present carriers.

In some carriers, the supply tray is disposed above the sample tray. The supply tray and the sample tray, in some carriers, each occupy at least 30% of the interior volume of the case.

The supply tray, in some carriers, defines a plurality of supply compartments. At least one of the supply compartments of the supply tray, in some carriers, is configured to receive one or more needles. In some carriers, at least one of the supply compartments of the supply tray is configured to receive one or more wipes and/or one or more bandages. Two or more of the supply compartments of the supply tray, in some carriers, each have a transverse dimension that is between 12 and 20 millimeters (mm) such that the supply compartment is configured to hold a collection tube.

Some kits comprise a plurality of supplies disposed in the supply compartments of the supply tray. The supplies, in some kits, include one or more collection tubes. In some kits, the supplies include one or more needles, the needle(s) optionally including one or more butterfly needles and/or one or more needles having a gauge that is between 18 and 25. The supplies, in some kits, include one or more wipes, the wipe(s) optionally including one or more sanitizing wipes. In some kits, the supplies include one or more collection tubes. In some kits, at least one of the collection tubes has a diameter that is between 10 and 17 millimeters (mm).

The sample tray, in some carriers, defines one or more, optionally two or more, sample compartments and comprises a thermally insulative material. The thermally-insulative material, in some carriers, has a thermal conductivity that is less than or equal to 0.10 W/m·K.

In some carriers, the case comprises a flap movable between a closed position in which the interior volume of the case is enclosed and an open position in which the interior volume of the case is accessible through an opening defined by the case. An interior surface of the flap that faces the interior volume of the case when the flap is in the closed position, in some carriers, is configured to hold one or sheets of paper, one or more portable electronic devices, and/or one or more writing utensils.

Some carriers comprise a sharps container. The sharps container, in some carriers, is removably coupled to an exterior of the case. In some carriers, the sharps container comprises a material that complies with ASTM F2132-01 (2010).

Some carriers comprise a gloves pocket. The gloves pocket, in some carriers, is fixed to an exterior of the case. In some carriers, the gloves pocket comprises a slit. The gloves pocket, in some carriers, is configured to receive a plurality of gloves such that each of the gloves is removable from the gloves pocket through the slit. Some kits comprise a plurality of liquid-impermeable gloves. The liquid-impermeable gloves, in some kits, are disposed in the gloves pocket and are removable from the gloves pocket through the slit.

Some carriers comprise at least two wheels coupled to a bottom of the case. Some carriers comprise a handle coupled to the case and movable between a first position and a second position. In some carriers, the handle is disposed further from a top of the case when the handle is in the second position than when the handle is in the first position.

Some carriers comprise an electric power supply. Some carriers comprise a receptacle in electrical communication with the power supply. Some kits comprise a centrifuge configured to be electrically coupled to the receptacle.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified—and includes what is specified; e.g., substantially 90 degrees includes 90 degrees and substantially parallel includes parallel—as understood by a person of ordinary skill in the art. In any disclosed embodiment, the terms "substantially," "about," and "approximately" may be substituted with "within [a percentage] of" what is specified, where the percentage includes 0.1, 1, 5, and 10 percent.

The terms "comprise" and any form thereof such as "comprises" and "comprising," "have" and any form thereof such as "has" and "having," and "include" and any form thereof such as "includes" and "including" are open-ended linking verbs. As a result, an apparatus that "comprises,"

"has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses and methods can consist of or consist essentially of—rather than comprise/include/have-any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a device or system that is configured in a certain way is configured in at least that way, but it can also be configured in ways other than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 4E illustrates a paper and writing utensils held by the flap, a needle being placed in a sharps container coupled to the case, and a glove being removed from a gloves pocket coupled to the case.

DETAILED DESCRIPTION

Figure 1A:
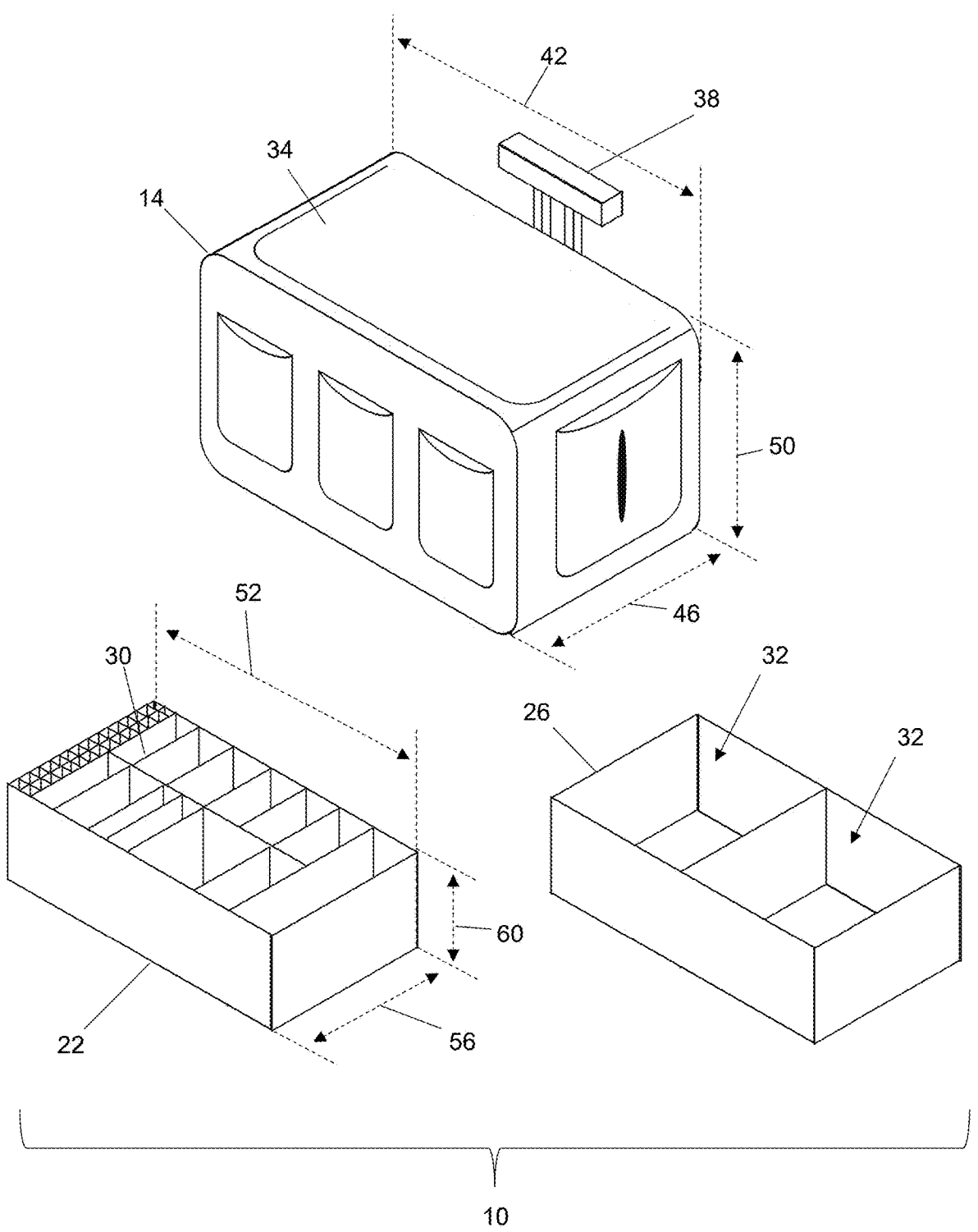
FIG. 1A is a perspective view of an embodiment of the present carriers that includes a case, a supply tray, and a sample tray.
Figure 1B:
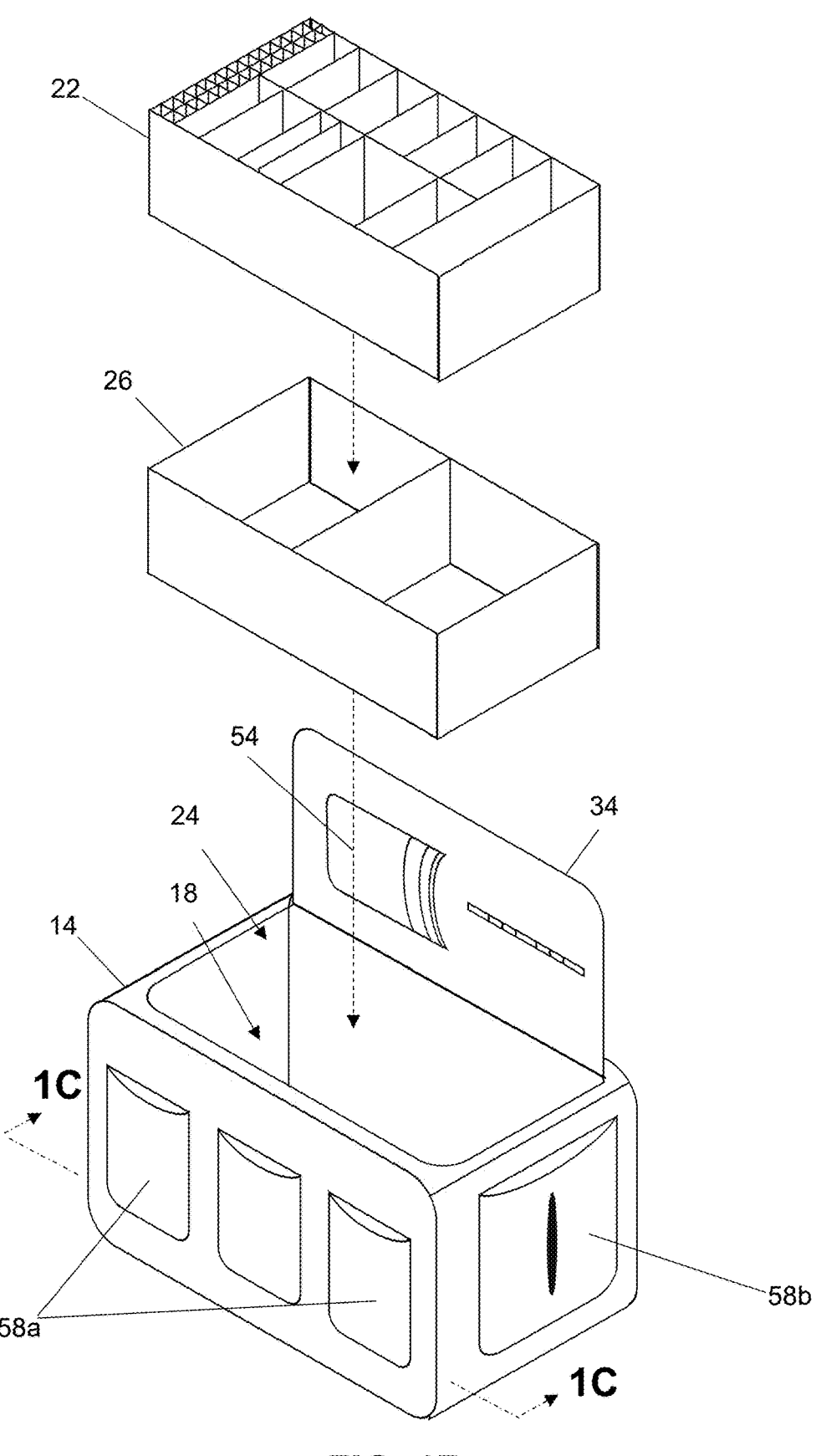
FIG. 1B is a perspective view of the carrier of FIG. 1A with the flap of the case in the open position, and illustrates how the supply tray and the sample tray are receivable in the interior volume of the case.
Figure 1C:
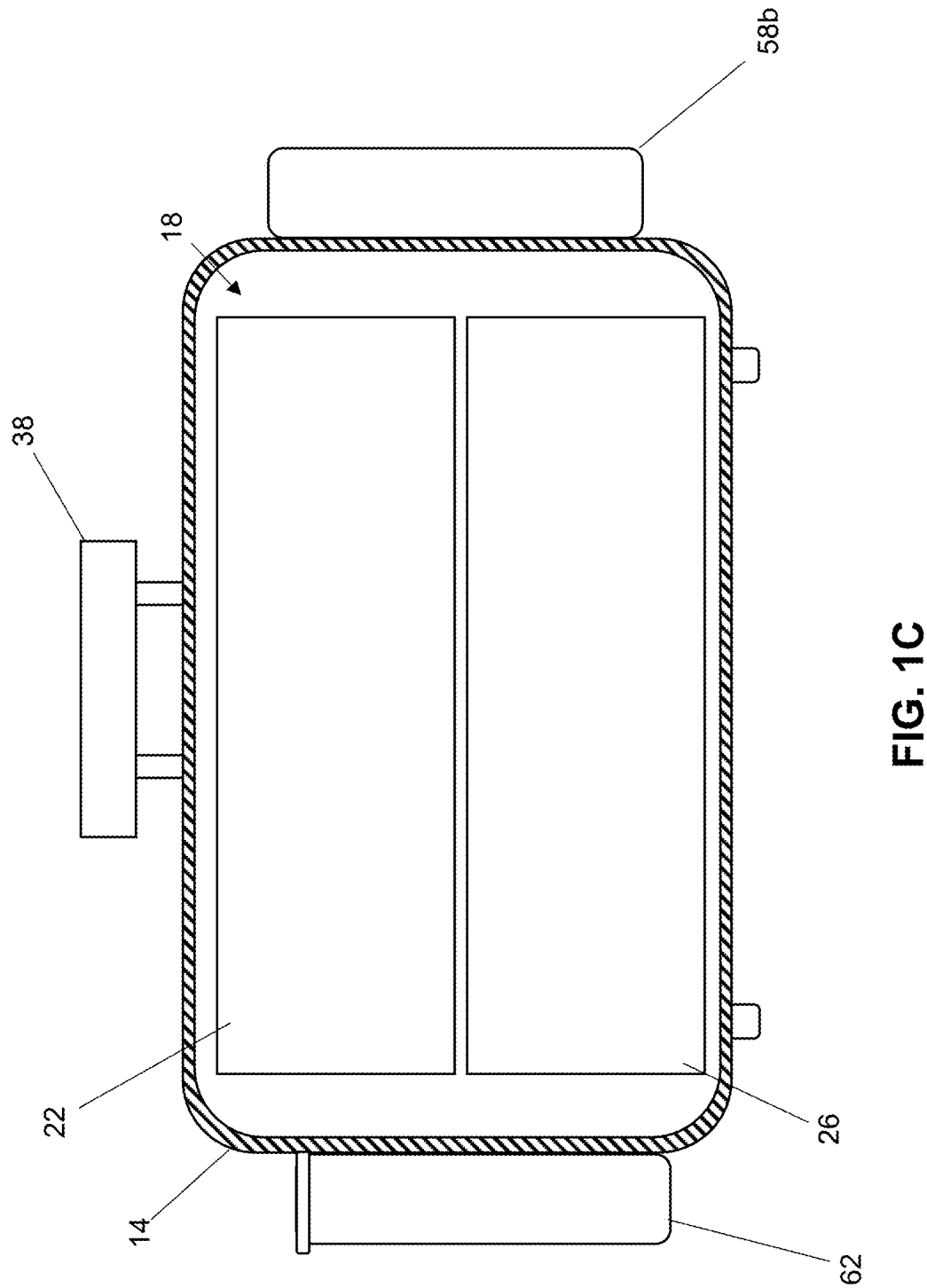
FIG. 1C is a sectional view of the carrier of FIG. 1A taken along line 1C-1C in FIG. 1B and illustrates the supply tray and the sample tray disposed in the interior volume of the case.

Referring to FIGS. 1A-1C, shown is an embodiment 10 of the present carriers. Carrier 10 can comprise a case 14 that defines an interior volume 18 configured to receive a supply tray 22 and a sample tray 26, which can each be removably coupled to the case in the interior volume (FIGS. 1B and 1C). For example, to permit supply tray 22 and sample tray 26 to be inserted into and removed from interior volume 18, case 14 can comprise a flap 34 that can be movable between a closed position in which the interior volume of the case is enclosed (FIGS. 1A and 1C) and an open position in which the interior volume of the case is accessible through an opening 24 defined by the case (FIG. 1B). Supply tray 22 and sample tray 26 can each be inserted into or removed from interior volume 18 through opening 24 when flap 34 is in the open position, and the supply tray and the sample tray can be enclosed in the interior volume when the flap is in the closed position (e.g., in which a zipper couples the flap to a shell of the case) for transport. Supply tray 22 and sample tray 26 can rest freely in interior volume 18, or carrier 10 can include one or more mechanisms, such as one or more latches, configured to releasably engage the supply tray and the sample tray when they are in the interior volume to hold them in place.

Carrier 10 can be configured to carry both supplies for obtaining biological samples and the biological samples after they are collected. To do so, carrier 10's supply tray 22 can define a plurality of supply compartments 30, such as greater than or equal to any one of, or between any two of, 1, 2, 3, 4, 5, 6, 7, 8, 9, 10, 15, 20, 30, or 40 supply compartments, that can be configured to hold supplies such as one or more collection tubes, needles, bandages, wipes, and/or the like as described in further detail below with reference to FIGS. 2A-2C. And carrier 10's sample tray 26 can define one or more sample compartments 32, such as greater than or equal to any one of, or between any two of, 1, 2, 3, 4, or 5 (e.g., two or more) sample compartments, that can be configured to hold one or more biological samples as described below with reference to FIGS. 3A-3C. As shown, supply tray 22 can be disposed above sample tray 26 when they are in case 14's interior volume 18, which allows the supplies in the supply tray to be readily accessed without removing the supply tray from the interior volume (e.g., with flap 34 in the open position), if desired. Furthermore, supply tray 22 and sample tray 26 can each be rigid to support the supplies and samples, facilitate insertion into and removal from interior volume 18, and allow the supply tray and sample tray to be used as a secure working area when they are removed from the interior volume during sample collection.

Carrier 10 can be relatively compact to facilitate transportability, while being large enough to hold supplies and biological samples. For example, case 14 can have a length 42 that is less than or equal to any one of, or between any two of, 36, 32, 28, 24, 20, 16, 12, or 8 inches (e.g., between 16 and 32 inches, such as between 18 and 22 inches); a width 46, measured perpendicularly to the length 42, that is less than or equal to any one of, or between any two of, 24, 20, 16, 15, 14, 13, 12, 11, 10, 9, 8, 7, 6, 5, or 4 inches (e.g., between 10 and 14 inches); and a height 50, measured perpendicularly to length 42 and width 46, that is less than or equal to any one of, or between any two of, 24, 20 16, 15, 14, 13, 12, 11, 10, 9, 8, 7, 6, 5, or 4 inches (e.g., between 10 and 14 inches). These dimensions are provided by way of illustration and are non-limiting.

Supply tray 22 and sample tray 26 can be sized to collectively occupy most, up to and including substantially all, of interior volume 18 such that the supply tray and sample tray each have a relatively large carrying capacity. For example, supply tray 22 and sample tray 26 can each occupy greater than or equal to any one of, or between any two of, 25%, 30%, 35%, 40%, or 45% of case 14's interior volume 18 such that the trays can collectively occupy greater than or equal to any one of, or between any two of, 50%, 60%, 70%, 80%, or 90% of the interior volume. As shown, supply tray 22 and sample tray 26 can each have a length 52 and width 56 that are substantially the same as (but still smaller than) length 42 and width 46, respectively of case 14 such that the trays can fit therein; for example, supply tray 22 and sample tray 26 can each have a length 52 that is less than or equal to any one of, or between any two of, 32, 28, 24, 20, 16, 12, or 8 inches (e.g., between 12 and 31 inches, such as between 14 and 21 inches) and a width 56 that is less than or equal to any one of, or between any two of, 22, 18, 16, 15, 14, 13, 12, 11, 10, 9, 8, 7, 6, 5, or 4 inches (e.g., between 6 and 13 inches). With supply tray 22 disposed above sample tray 26 in interior volume 18, the supply tray and sample tray can each have a height 60 that less than or equal to about half of case 14's height 50 to allow the trays to fit therein, such as a height that is less than or equal to any one of, or between any two of, 12, 10, 9, 8, 7, 6, 5, 4, 3, or 2 inches (e.g., between 4 and 7 inches).

Figures 2A, 2B:
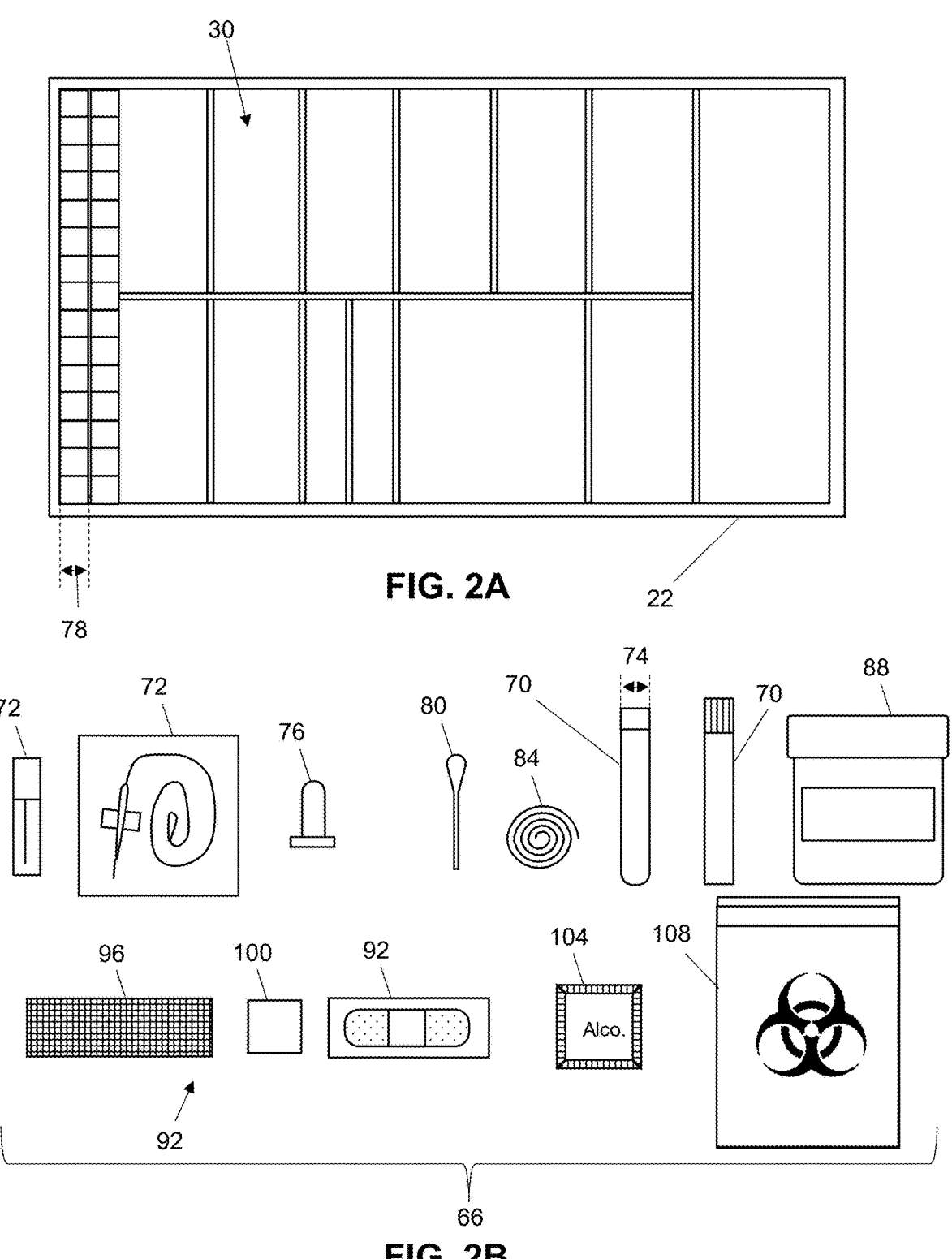
FIG. 2A is a top view of the supply tray of the carrier of FIG. 1A.
FIG. 2B shows supplies that the supply tray of the carrier of FIG. 1A can hold and that some of the present kits can comprise.
Figure 2C:
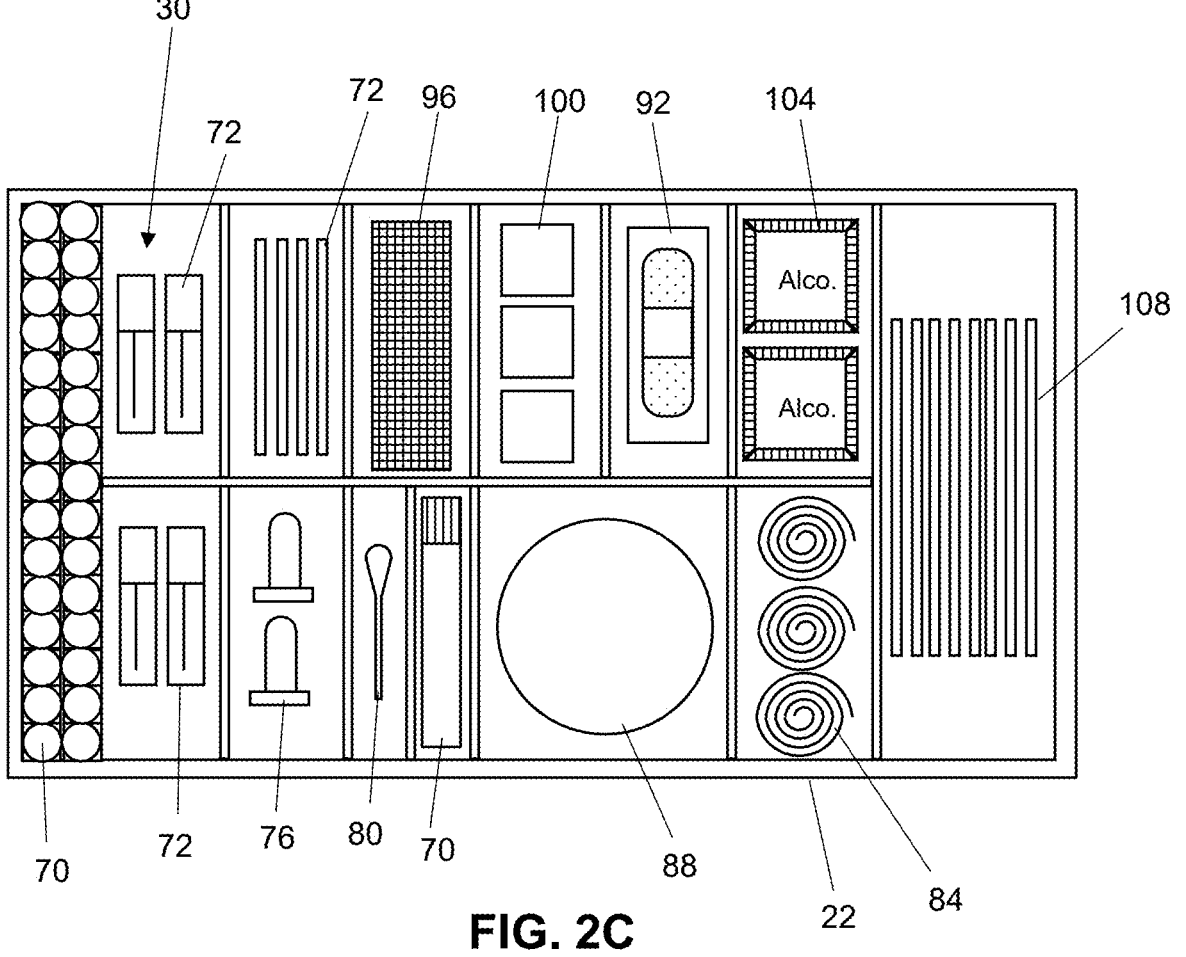
FIG. 2C is a top view of the supply tray of the carrier of FIG. 1A with the supplies of FIG. 2B disposed in the compartments of the supply tray.

Referring to FIGS. 2A-2C, supply compartments 30 can be sized and shaped to hold and organize various supplies 66 for collecting biological samples such as blood, stool, urine, and/or the like. For example, supply compartments 30 can be configured to hold one or more, optionally two or more, needles 72 (e.g., while the needle(s) are disposed in packaging), caps 76, tourniquets 84, collection tubes 70, bandages 92, and/or wipes 104 for collecting blood from an individual. Wipe(s) 104 can each include one or more sanitizing wipes (e.g., in which the wipe contains alcohol) to sanitize the draw site and mitigate the risk of infection, while tourniquet(s) 84 can be used to distend the individual's vein for a blood draw into one of collection tube(s) 70 using one of needle(s) 72. As shown needle(s) 72 that supply compartments 30 can hold can include one or more standard needles having a gauge that is greater than or equal to any one of, or between any two of, 18, 19, 20, 21, 22, 23, 24, 25, 26 (e.g., between 18 and 25 gauge, such as between 21 and 25 gauge) and/or one or more butterfly needles. And collection tube(s) 70 that supply compartments 30 can hold can include any suitable collection tubes, such as one or more Vacutainers®, and can each have a transverse dimension 74 (e.g., a diameter) that is greater than or equal to any one of, or between any two of, 10, 11, 12, 13, 14, 15, 16, 17, 18, 19, or 20 mm (e.g., between 10 and 17 mm, such as about 13 mm or about 16 mm) and/or have an interior volume that is greater than or equal to any one of, or between any two of, 3, 4, 5, 6, 7, 8, 9, or 10 mL. Bandage(s) 92 that supply compartments 30 can hold can include any suitable bandages to prevent bleeding from the draw site, such as an adhesive bandage and/or gauze 100 (e.g., a gauze pad and/or roll) that is optionally paired with self-adherent wrap 96 to secure the pad to the draw site.

Supply compartments 30 can also hold one or more, optionally two or more, pipettes 80, specimen containers 88, and/or biohazard bags 108 to permit the collection of other biological samples such as stool and/or urine. For example, specimen container(s) 88 that supply compartments 30 can hold can have an interior volume that is greater than or equal to any one of, or between any two of, 100, 120, 140, 160, 180, 200, 250, 300, 350, 400, 450, or 500 mL to accommodate a stool or urine sample.

To organize supplies 66 for efficient access thereto, each of supply compartments 30 can be configured to receive one category of the supplies. For example, supply compartments 30 can include at least one supply compartment configured to receive one or more collection tubes 70, at least one supply compartment configured to receive one or more needles 72, at least one supply compartment configured to receive one or more caps 76, at least one supply compartment configured to receive one or more pipettes 80, at least one supply compartment configured to receive one or more tourniquets 84, at least one supply compartment configured to receive one or more specimen containers 88, at least one supply compartment configured to receive one or more bandages 92 (or at least a portion thereof, such as self-adherent wrap 96 or gauze 100), at least one supply compartment configured to receive one or more wipes 104, and/or at least one supply compartment configured to receive one or more biohazard bags 108.

As an illustration, two or more (e.g., ten or more) of supply compartments 30 can each be sized to hold a single collection tube 70, e.g., with a transverse dimension that is substantially the same as that of the collection tube, such as a transverse dimension that is greater than or equal to any one of, or between any two of, 10, 11, 12, 13, 14, 15, 16, 17, 18, 19, or 20 mm (e.g., between 10 and 20 mm), and can each be adjacent to at least one other of the collection-tube-holding supply compartments, while the remainder of the supply compartments can be larger than those that hold the collection tubes. With this configuration, supply compartments 30 that hold collection tubes 70 can do so with the collection tubes in an upright position such that the caps of the collection tubes—which may be color-coded based on the use of the collection tube—are visible to be readily identified. And a user (e.g., a phlebotomist) can use each of collection-tube-holding supply compartments 30 to hold a collection tube 70 both before and after a biological sample (e.g., blood) is collected therein; this promotes efficiency in sample collection by allowing the user to temporarily store the collection tube on the supply tray while taking other samples, if needed, before moving the collection tube (and any other sample-containing vessels) to one of sample compartment(s) 32.

Any of the present kits can include any of the present containers with one or more supplies 66 (e.g., any of those described above) disposed in supply compartments 30 as described above.

Figure 3A:
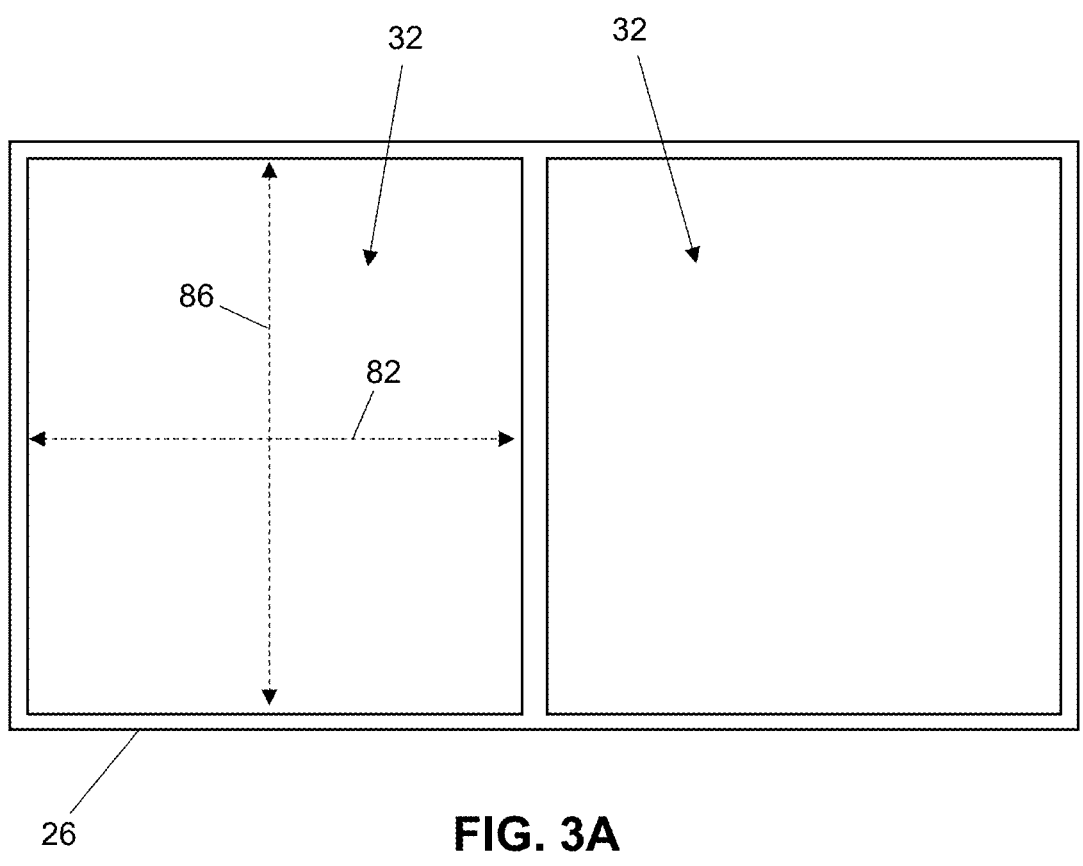
FIG. 3A is a top view of the sample tray of the carrier of FIG. 1A.
Figure 3B:
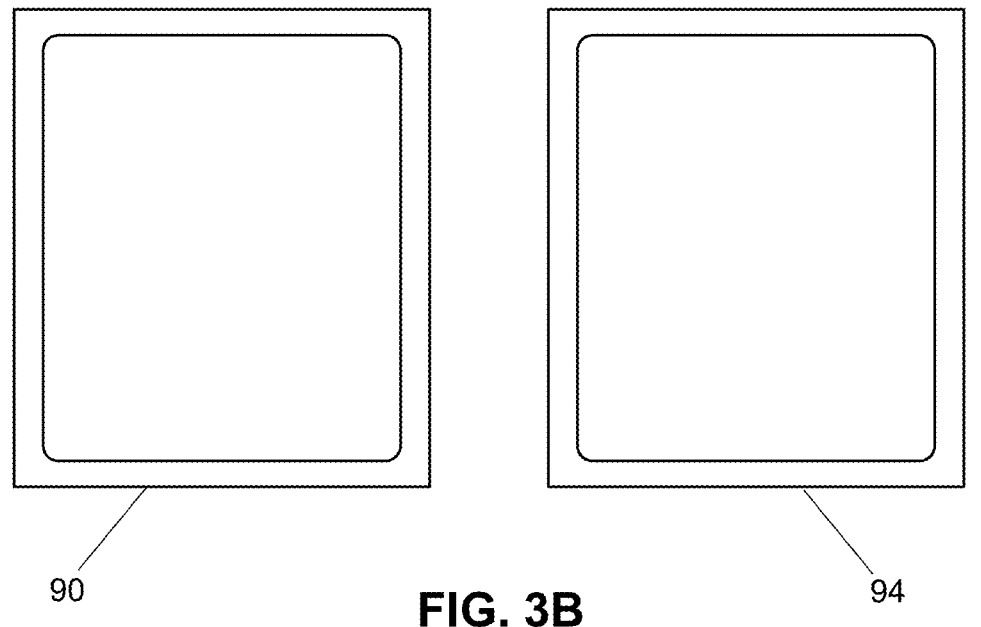
FIG. 3B is a top view of a cooling pack and a heating pack that the sample tray of the carrier of FIG. 1A can hold and that some of the present kits can comprise.
Figure 3C:
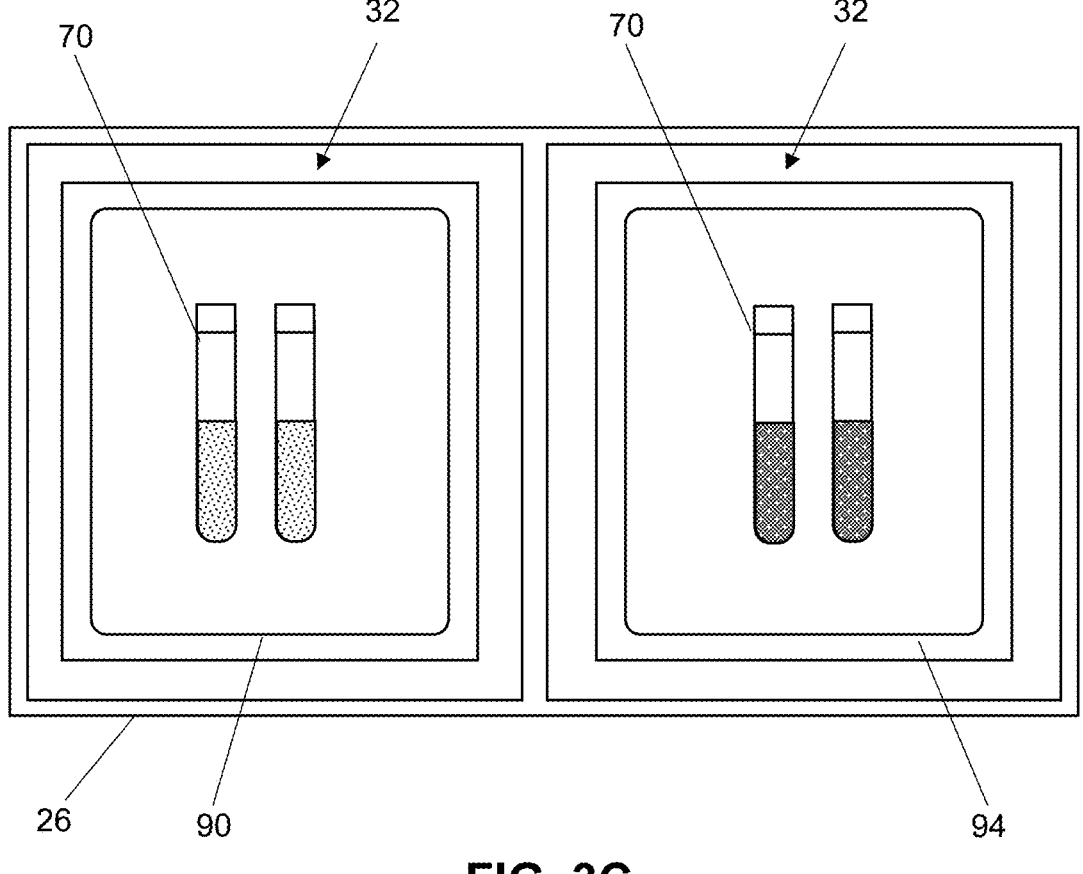
FIG. 3C is a top view of the sample tray of the carrier of FIG. 1A with the cooling and heating packs of FIG. 3B and collection tubes disposed in the compartments of the sample tray.

Referring to FIGS. 3A-3C, sample tray 26 can be configured to hold and preserve biological samples for transport (e.g., can be configured to hold collection tube(s) 70 and/or specimen container(s) 88, optionally in biohazard bag(s) 108, that contain the biological samples). To do so, sample tray 26 can comprise a thermally-insulative material to mitigate heat transfer into and/or out of sample compartment (s) 32. The thermally-insulative material can have a thermal conductivity that is less than or equal to any one of, or between any two of, 0.75, 0.50, 0.25, 0.10, 0.05, 0.04, or 0.03 W/m·K (e.g., less than or equal to 0.10 W/m·K). For example, the thermally-insulative material can comprise a polymer and/or foam (e.g., foam layered between inner and outer polymer shells), such as acetal (i.e., polyoxymethylene), polyethylene, polyurethane, polystyrene, and/or the like. Such materials can, in addition to mitigating heat transfer, allow sample tray 26 to be rigid to support samples held therein and facilitate the sample tray's removal from and insertion into case 14 as described above. While as shown sample tray 26 has an open top, in other embodiments the sample tray can include a cover (e.g., comprising the thermally-insulative material) configured to enclose sample compartment(s) 32.

To maximize carrying capacity, sample compartment(s) 32 can collectively span approximately all of sample tray 26's length 52, width 56, and height 60. For example, if sample tray 26 includes two sample compartments 32, length 82 and width 86 of each sample compartment can be about half of length 52 and about width 56, respectively, of the sample tray, or can be about the length and about half of the width, respectively, of the sample tray. As an illustration, to readily accommodate samples (e.g., in collection tube(s) 70 and/or specimen container(s) 88), length 82 of each sample compartment 32 can be greater than or equal to any one of, or between any two of, 4, 6, 8, 10, 12, 14, or 16 inches (e.g., between 5 and 15 inches, such as between 6 and 9 inches) and a width 86 that is greater than or equal to any one of, or between any two of, 3, 4, 5, 6, 7, 8, 9, 10, 11, 12, 13, 14, 15, 16, 17, 18, 19, 20, or 21 inches (e.g., between 5 and 12 inches).

For sample preservation, each of sample compartment(s) 32 can hold—and some of the present kits can include—one or more cooling packs 90 and/or one or more heating packs 94 to maintain a temperature in the sample compartment that is below or above, respectively, the ambient temperature (FIG. 3B). Each cooling pack 90 can comprise, for example, an enclosure containing a liquid or gel medium having a freezing point that is less than or equal to any one of, or between any two of, 20, 15, 10, 5, 0, −5, −10, or −20° C. (e.g., less than or equal to 0° C.); the cooling pack can be cooled (e.g., frozen) and inserted into the sample compartment to lower the temperature therein (e.g., to the freezing point of the cooling pack) for sample preservation. Each heating pack 94 can comprise, for example, an enclosure containing a medium configured to release heat when activated, such as a solution of sodium acetate that releases heat when crystallized into a hydrated salt after activation causes crystals of sodium acetate to be released into the solution, or a mixture of cellulose, iron, activated carbon, vermiculite, and salt that, when exposed to air, results in oxidation of the iron to release heat; such heating may be suitable for samples that should be stored above ambient temperature. Additionally or alternatively, carrier 10 can include a cooler and/or a heater (e.g., powered by the below-described electric power supply 98) configured to remove heat from or add heat to, respectively, at least one of sample compartment(s) 32.

The use of two or more sample compartments 32 can allow for storage of different biological samples at different temperatures. For example, biological samples that should be cooled can be stored in a first one of sample compartments 32 (e.g., with cooling pad 90) and biological samples that should be heated can be stored in a second one of the sample compartments (e.g., with heating pad 94) (FIG. 3C).

As another example, if the different biological samples should all be cooled but maintained at a different temperature, a first set of the biological samples can be stored in a first one of sample compartments 32 with a cooling pad 90 whose medium has a first freezing point and a second set of the biological samples can be stored in a second one of sample compartments 32 with a cooling pad whose medium has a second freezing point that is different than the first freezing point. In either case, the thermally-insulative material of sample tray 30 can mitigate heat transfer between the different sample compartments 32 to promote maintenance of their respective temperatures.

Figures 4A, 4B, 4C, 4D:
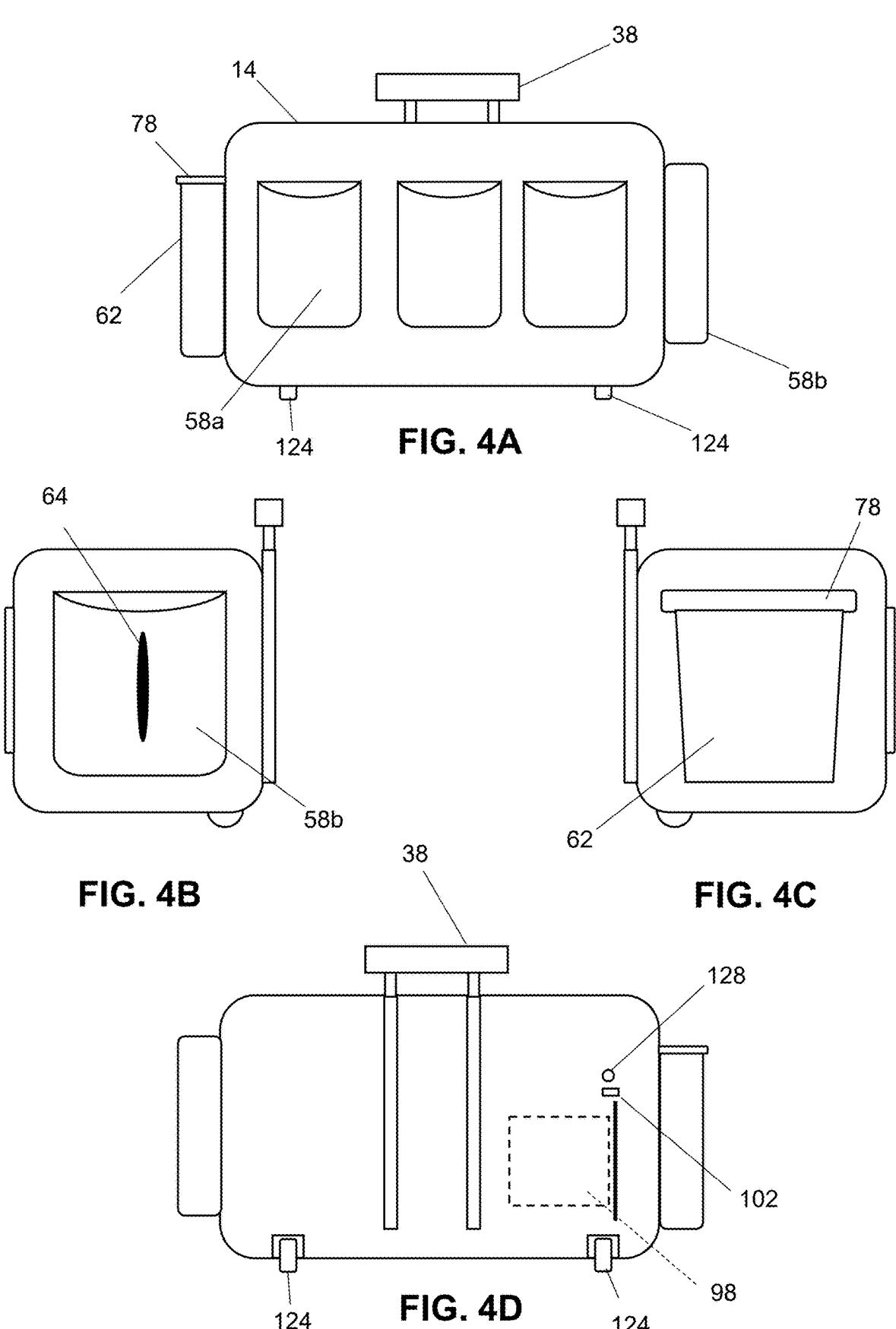
FIGS. 4A-4D are front, right, left, and rear views, respectively, of the case of the carrier of FIG. 1A.
Figure 4E:
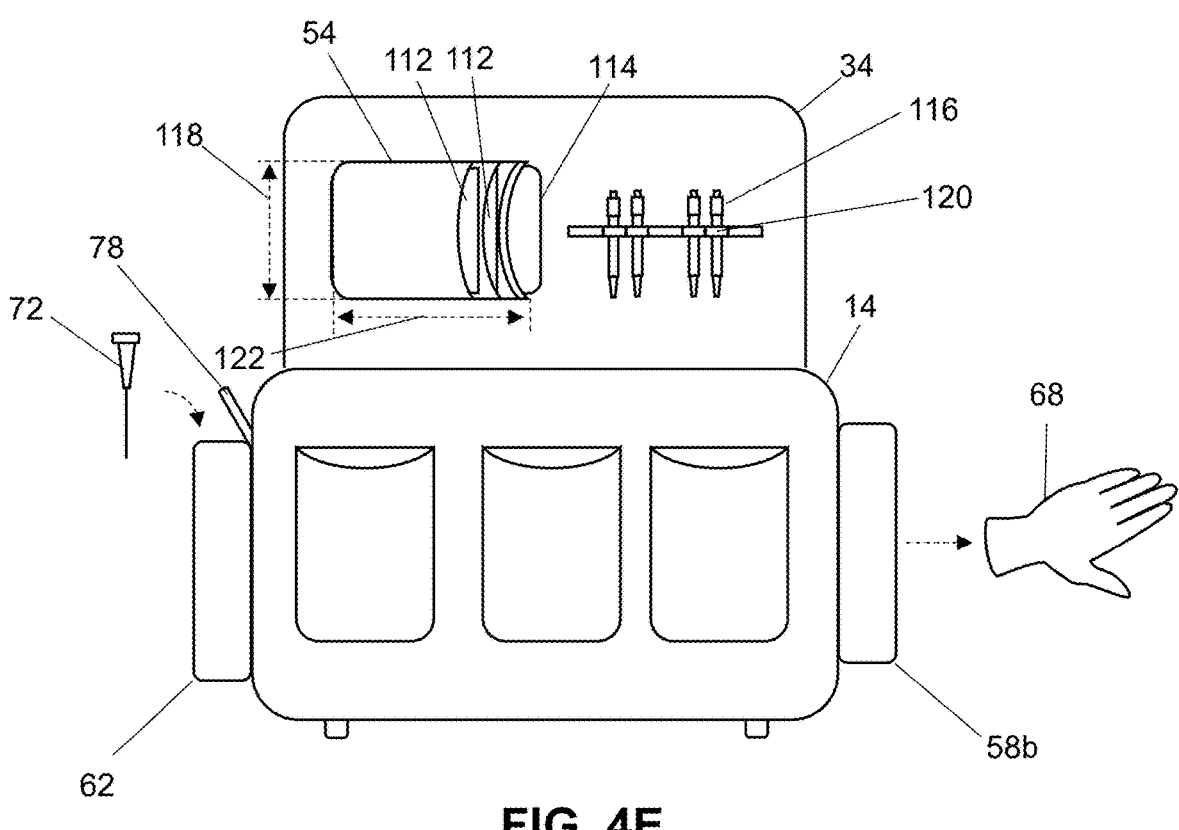
FIG. 4E is a front view of the case of the carrier of FIG. 1A with the flap in the open position.

Referring to FIGS. 4A-4H, carrier 10 can comprise additional features to facilitate the transport, collection, and handling of biological samples. For example, to hold additional materials, carrier 10 can include one or more pockets (e.g., 58a and 58b) that are fixed to an exterior of case 14. One or more, optionally two or more (e.g., three), pockets 58a can be fixed to a front face of case 14 to hold one or more accessories (FIG. 4A). The pocket(s) can also include a gloves pocket 58b (which can be fixed to, for example, a side face of case 14) comprising a slit 64 (FIGS. 4A and 4B). Gloves pocket 58b can be configured to receive—and, in some of the present kits, can hold—a plurality of liquid-impermeable gloves 68 (e.g., latex, rubber, /or nitrile gloves) for a user to wear during sample collection, which can each be removable from the gloves pocket through slit 64 (FIG. 4E).

Figure 4F:
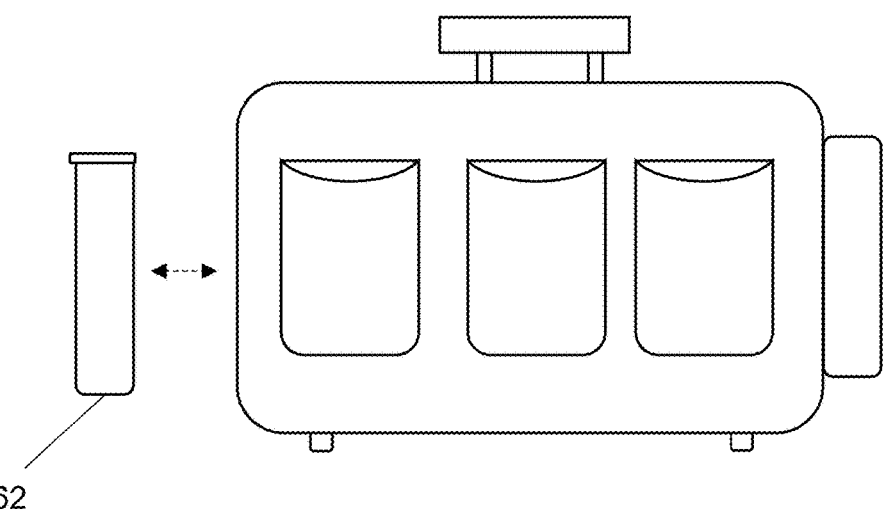
FIG. 4F is a front view of the case of the carrier of FIG. 1A and illustrates how the sharps container is removably coupled to the case.
Figure 4G:
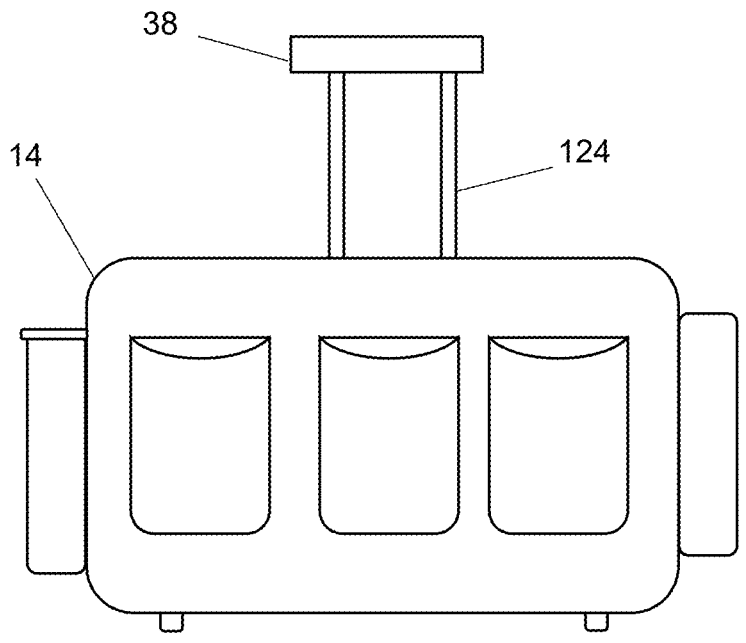
FIG. 4G is a front view of the case of the carrier of FIG. 1A with a handle of the case extended from its first, stowed position to its second, deployed position.
Figure 4H:
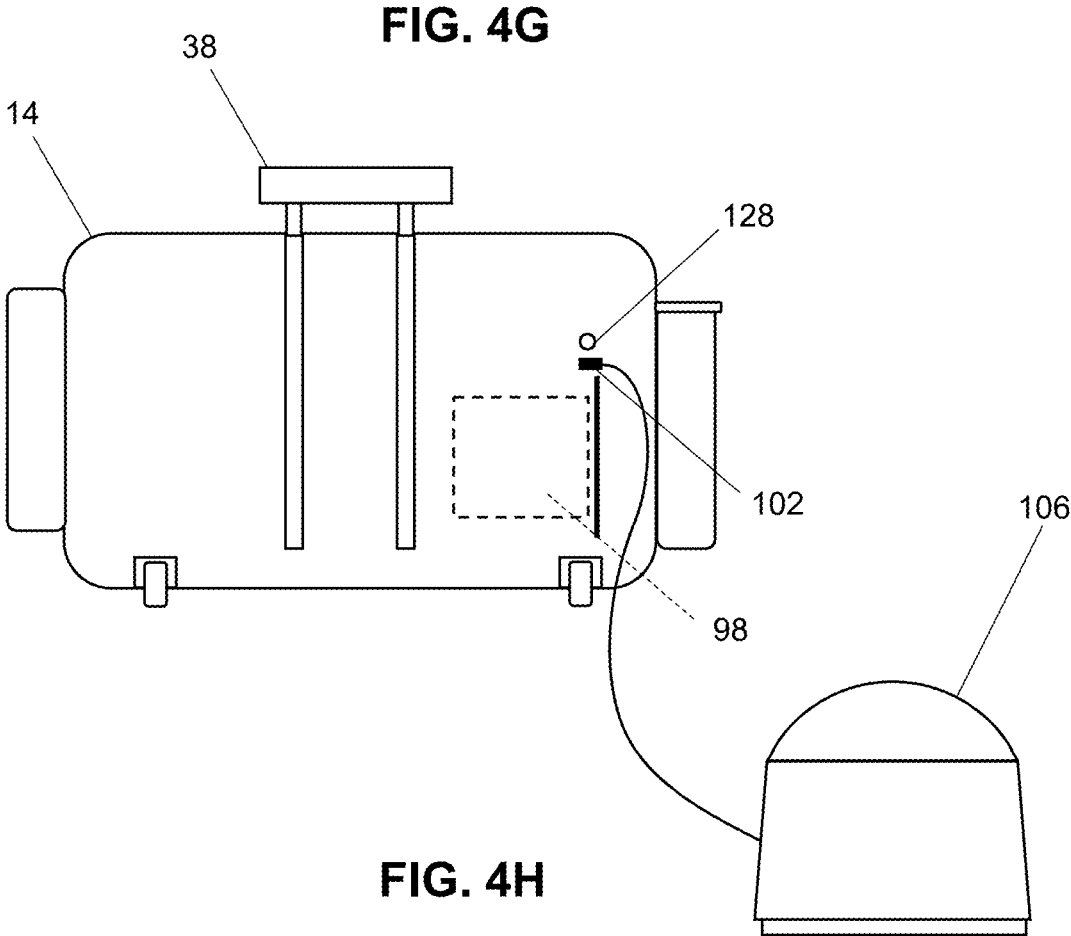
FIG. 4H is a rear view of the case of the carrier of FIG. 1A with a centrifuge electrically coupled to a receptacle of the carrier that is in electrical communication with an electric power source of the carrier.

Additionally, carrier 10 can comprise a sharps container 62, which can be removably coupled to the exterior of case 14 (e.g., to a side face of the case, such as the side face opposing the side face that the gloves pocket is fixed to) (FIGS. 4A and 4C). Sharps container 62 can be configured to safely receive each of needle(s) 72 after the needle is used to collect a biological sample (e.g., blood); for example, the container can comprise a puncture-resistant material, such as a material that complies with ASTM F2132-01 (2010), and can have a lid 78 movable between a closed position in which an interior volume of the sharps container is enclosed (FIG. 4A) and an open position in which the needle can be placed in the sharps container's interior volume (FIG. 4E). To facilitate safe disposal of needle(s) 72 after all biological samples are collected, sharps container 62 can be removed from case 14 (FIG. 4F).

Carrier 10 can also be configured to hold one or more sheets of paper 112 (e.g., letter-sized (8.5 inches×11 inches) or A4-sized (8.3×11.7 inches) sheets of paper) that may include, for example, paperwork the user may need for sample collection, one or more writing utensils 116 (e.g., one or more pens, pencils, markers, and/or the like), and/or one or more portable electronic devices 114 such as a laptop or tablet. As shown, an interior surface of case 14's flap 34 that faces the case's interior volume 18 when the flap is in the closed position can be configured to do so, such as with one or more pockets 54 that are each configured to receive sheet(s) of paper 112 and/or a portable electronic device 114 and one or more loops 120 that are each configured to hold a single writing utensil 116 (FIG. 4E). To illustrate, at least one—up to and including each—of pocket(s) 54 can have a width 118 that is greater than or equal to any one of, or between any two of, 8, 9, 10, 11, 12, 13, 14, or 15 inches (e.g., between 9 and 13 inches) and a length 122 that is greater than or equal to any one of, or between any two of, 10, 11, 12, 13, 14, 15, 16, 17, 18, 19, or 20 inches (e.g., between 11 and 18 inches) to accommodate sheet(s) of paper 112 or a portable electronic device 114 like a laptop.

To allow a user to easily transport carrier 10, the carrier can include at least two wheels 124 coupled to the bottom of case 14 such that the carrier can be rolled along a ground surface (FIGS. 4A and 4D). Furthermore, carrier 10 can include a handle 38 that is coupled to case 14 and is movable between a first position (FIG. 4A) and a second position (FIG. 4G) (e.g., via one or more, optionally two or more, telescoping arms 124 that couple the handle to the case). Handle 38 can be disposed further from a top of case 14 when the handle is in the second position than when the handle is in the first position, which allows a user to readily grip the handle to roll carrier 10 when the grip is in the second, deployed position and to collapse the grip to the first, stowed position for compact storage. Additionally or alternatively, carrier 10 can include one or more, optionally two or more, shoulder straps coupled to the exterior of case 14 (e.g., to a back face of the case) that can be placed around the arms of the user so the user can wear the carrier on the user's back (e.g., as a backpack); the carrier can also include one or more supports straps to promote weight distribution and thus comfort, such as one or more supports straps configured to extend between and couple multiple shoulder straps together (e.g., across the chest of a user wearing the carrier) and/or one or more support straps at a bottom of the case that are configured to encircle the user's waist.

Carrier 10 can also include an electric power supply 98 (e.g., a battery), which can be coupled to case 14. Electric power supply 98 can be in electrical communication with a receptacle 102 that can be coupled to case 14, which can be configured to receive a plug from an electronic device such that the electric power supply can power the electronic device. For example, receptacle 102 can be configured to be electrically coupled to—and some of the present kits can comprise—a centrifuge 106, which can be used to process one or more of the biological samples (e.g., that are disposed in collection tube(s) 70 that can be received in the centrifuge) (FIG. 4H); in this manner, a user can employ electric power supply 98 to run the centrifuge rather than relying on, for example, the battery of the user's automobile, thereby mitigating the risk of draining the automobile battery. Electric power supply 98 can also be configured to power a cooler and/or heater—if included—to cool or heat, respectively, one or more of sample compartment(s) 32 as described above. Electric power supply 98 can be removably coupled to case 14 (e.g., in a pocket of the case) so that it can be removed for charging. Additionally or alternatively, carrier 10 can include a charging receptacle 128 that is in electrical communication with electric power supply 98 and can be electrically coupled to another power source to charge the electric power supply.

Some of the present methods of collecting a biological sample can be performed using any of the present carriers (e.g., 10) and any of the present kits comprising a case (e.g., 14), supply tray (e.g., 22), and sample tray (e.g., 26). Some methods comprise removing one or more supplies (e.g., 66) from the supply compartments (e.g., 30) of the supply tray. For example, to collect one or more blood samples, some methods comprise removing a needle (e.g., 72), a tourniquet (e.g., 84), a collection tube (e.g., 70), a bandage (e.g., 92), and/or a wipe such as a sanitizing wipe (e.g., 104) from the supply compartments. Some methods include wrapping the tourniquet around an arm of a human subject (e.g., to distend a vein of the subject), wiping a draw site on the arm with the wipe (e.g., with the sanitizing wipe to sanitize the draw site), and inserting the needle through the draw site and into the vein of the subject. The needle can be placed in fluid communication with the collection tube such that blood flows from the vein of the subject into the collection tube (e.g., after removing the tourniquet). In some methods, multiple blood samples can be taken from the subject (e.g., for different tests); in such methods, one or more additional collection tubes can each be placed in fluid communication with the needle such that blood flows from the vein of the subject into the additional collection tube, or the above process can be repeated with an additional needle. Each of the collection tube(s) can be disposed in one of the supply compartments (e.g., the supply compartment that the collection tube was removed from) after blood is collected therein (e.g., for temporary storage thereof). After blood collection, some methods comprise applying the bandage (e.g., gauze (e.g., 100), optionally with self-adherent wrap (e.g., 96) wrapped around the subject's arm and the gauze, or an adhesive bandage) to the draw site and placing the removed needle(s) into a sharps container (e.g., 62) that is removably coupled to the case.

Some methods comprise collecting one or more urine and/or stool samples from the subject. Such methods can comprise removing one or more, optionally two or more, specimen containers (e.g., 88) from the supply compartments of the supply tray, removing a lid of the each of the specimen container(s), and receiving urine or stool into each of the specimen container(s); this collection can be performed by the subject, optionally with assistance from the user (e.g., the phlebotomist).

Some methods comprise removing two or more liquid-impermeable gloves (e.g., 68) from a gloves pocket (e.g., 58*b*) fixed to an exterior surface of the case (e.g., through a slit (e.g., 64) of the gloves pocket). The user can place one of the gloves on each hand of the user for protection during sample collection.

The supplies can be removed from the supply compartments when the supply tray is removably coupled to the case in the case's interior volume (e.g., 18) or when the supply tray is removed from the case's interior volume. In either case, some methods comprise removing the supply tray and, optionally, the sample tray from the interior volume of the case to provide access to the one or more sample compartments (e.g., 32) of the sample tray. Some methods comprise placing each of the collection tube(s) and/or the specimen container(s) that contain a biological sample (e.g., blood, urine, and/or stool) in one of the sample compartments, which optionally contains a cooling pack (e.g., 90) or a heating pack (e.g., 94) such that a temperature in the sample compartment is below or above, respectively, ambient temperature. Each of the collection tube(s) and/or specimen container(s) that contain a biological sample can be placed in a biohazard bag (e.g., 108) before being placed in one of the sample compartment(s). With sample collection and storage complete, some methods comprise removably coupling the supply tray and the sample tray to the case in the interior volume (e.g., with the biological sample(s) disposed in the sample compartment(s) of the sample tray), with the supply tray disposed above the sample tray.

Some methods comprise placing one or more of the collection tube(s) that contain a biological sample (e.g., blood) in a centrifuge and electrically coupling the centrifuge to a receptacle (e.g., 102) that is coupled to the case and is in electrical communication with an electric power supply (e.g., 98) of the carrier.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the apparatuses and methods are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A carrier for collecting biological samples, the carrier comprising:

a case that defines an interior volume;

a supply tray comprising a plurality of walls that define a plurality of supply compartments, the walls of the supply tray including:

outer walls that surround an interior space of the supply tray; and inner walls that are disposed in the interior space of the supply tray;

a sample tray that defines one or more sample compartments and comprises a thermally-insulative material; and a plurality of supplies that include one or more bandages, wherein each of the supplies is disposed in one of the supply compartments of the supply tray;

wherein:

the supply tray and the sample tray are each disposed in the interior volume of the case; and the case is configured to permit the supply tray and the sample tray to be removed from the interior volume of the case.

2. The carrier of claim 1, wherein the supply tray is disposed above the sample tray.

3. The carrier of claim 1, wherein the supply tray and the sample tray each occupy at least 30% of the interior volume of the case.

4. The carrier of claim 1, wherein the one or more sample compartments of the sample tray comprise two or more sample compartments.

5. The carrier of claim 1, wherein the thermally-insulative material has a thermal conductivity that is less than or equal to 0.10 W/m-K.

6. The carrier of claim 1, comprising a gloves pocket that:

is fixed to an exterior of the case;

comprises a slit; and is configured to receive a plurality of gloves such that each of the gloves is removable from the gloves pocket through the slit.

7. The carrier of claim 1, comprising:

at least two wheels coupled to a bottom of the case; and a handle coupled to the case and movable between a first position and a second position, wherein the handle is disposed further from a top of the case when the handle is in the second position than when the handle is in the first position.

8. The carrier of claim 1, comprising:

an electric power supply; and a receptacle in electrical communication with the power supply.

9. The carrier of claim 1, wherein the supplies include one or more needles, each of the needle(s) disposed in one of the supply compartments of the supply tray.

10. The carrier of claim 9, comprising a sharps container that:

is removably coupled to an exterior of the case; and comprises a material that complies with ASTM F2132-01 (2010).

11. The carrier of claim 1, wherein:

the case comprises a flap movable between a closed position in which the interior volume of the case is enclosed and an open position in which the interior volume of the case is accessible through an opening defined by the case; and an interior surface of the flap that faces the interior volume of the case when the flap is in the closed position is configured to hold:

one or more sheets of paper;

one or more portable electronic devices; and one or more writing utensils.

12. The carrier of claim 9, wherein the supplies include one or more collection tubes, each of the collection tube(s) disposed in one of the supply compartments of the supply tray.

13. The carrier of claim 12, wherein the one or more collection tubes comprise a plurality of collection tubes, each of the collection tubes disposed in a respective one of two or more of the supply compartments of the supply tray that each have a transverse dimension that is between 12 and 20 millimeters (mm).

14. The carrier of claim 9, wherein the one or more needles comprise one or more butterfly needles and/or one or more needles having a gauge that is between 18 and 25.

15. The carrier of claim 9, wherein the supplies include one or more wipes, each of the wipe(s) disposed in one of the supply compartments of the supply tray.

16. The carrier of claim 15, wherein the one or more wipes include one or more sanitizing wipes.

17. The carrier of claim 13, wherein the supplies include one or more sanitizing wipes, each of the sanitizing wipe(s) disposed in one of the supply compartments of the supply tray.

18. The carrier of claim 1, wherein the one or more bandages include:

an adhesive bandage; and a gauze pad and/or a gauze roll.

19. The carrier of claim 10, wherein the sharps container comprises a lid movable between a closed position in which an interior volume of the sharps container is enclosed and an open position in which one of the one or more needles can be placed in the interior volume of the sharps container.

20. The carrier of claim 1, wherein the supplies include one or more specimen containers and/or one or more biohazard bags that are each disposed in one of the supply compartments of the supply tray.

* * * * *